United States Patent
Sadaba Zubiri et al.

(10) Patent No.: US 10,343,986 B2
(45) Date of Patent: *Jul. 9, 2019

(54) PROCESS FOR PREPARING ESTERS OF LACTIC ACID, AND 2-HYDROXY-3-BUTENOIC ACID FROM SUGARS

(71) Applicant: Haldor Topsoe A/S, Kgs. Lyngby (DK)

(72) Inventors: Irantzu Sadaba Zubiri, Frederiksberg (DK); Esben Taarning, Frederiksberg (DK)

(73) Assignee: Haldor Topsoe A/S, Lyngby (DK)

( * ) Notice: Subject to any disclaimer, the term of this patent is extended or adjusted under 35 U.S.C. 154(b) by 8 days.

This patent is subject to a terminal disclaimer.

(21) Appl. No.: 16/133,146

(22) Filed: Sep. 17, 2018

(65) Prior Publication Data

US 2019/0016674 A1 Jan. 17, 2019

Related U.S. Application Data (63) Continuation of application No. 15/525,450, filed as application No. PCT/EP2015/076399 on Nov. 12, 2015, now Pat. No. 10,100,007.

(30) Foreign Application Priority Data

Nov. 28, 2014 (EP) .................................. 14195485
May 13, 2015 (DK) ............................... 2015 00288

(51) Int. Cl.
| | | |
|---|---|---|
| *C07C 319/18* | (2006.01) | |
| *C07C 67/44* | (2006.01) | |
| *C07C 67/475* | (2006.01) | |
| *C07C 67/00* | (2006.01) | |
| *C07C 69/68* | (2006.01) | |
| *C07C 69/732* | (2006.01) | |

(52) U.S. Cl.
CPC ............ *C07C 319/18* (2013.01); *C07C 67/00* (2013.01); *C07C 67/44* (2013.01); *C07C 67/475* (2013.01); *C07C 69/68* (2013.01); *C07C 69/732* (2013.01)

(58) Field of Classification Search
CPC ....... C07C 319/18; C07C 67/00; C07C 69/68; C07C 69/732
See application file for complete search history.

(56) References Cited

U.S. PATENT DOCUMENTS

| | | | |
|---|---|---|---|
| 4,792,620 A | 12/1988 | Paulik | |
| 8,143,439 B2 * | 3/2012 | Taarning | ................. C07C 51/00 560/179 |
| 2011/0229626 A1 | 9/2011 | Devaux et al. | |

FOREIGN PATENT DOCUMENTS

| | | |
|---|---|---|
| EP | 1 284 270 A1 | 2/2003 |
| EP | 2 184 270 A1 | 5/2010 |
| WO | WO 98/32735 A1 | 7/1998 |
| WO | WO 2015/024875 A1 | 2/2015 |
| WO | WO 2016/083137 A1 | 6/2016 |

OTHER PUBLICATIONS

Guo et al, ChemSusChem, Highly Active and Recyclable Sn-MWW Zeolite Catalyst for Sugar Conversion to Methyl Lactate and Lactic Acid, 2013, 6, pp. 1352-1356. (Year: 2013).*
M.S. Holm et al., "Conversion of Sugars to Lactic Acid Derivatives Using Heterogeneous Zeotype Catalysts", Science, vol. 328, Apr. 30, 2010, pp. 602-605.
Q. Guo et al., "Highly Active and Recyclable Sn-MWW Zeolite Catalyst for Sugar Conversion to Methyl Lactate and Lactic Acid", Chemsuschem, vol. 6, No. 8, Jun. 17, 2013, pp. 1352-1356.
E. Treister et al., "Major Galaxy Mergers and the Growth of Supermassive Black Holes in Quasars", Science, vol. 328, No. 5978, Mar. 25, 2010, pp. 1-17.
Norskov et al., "Nature Chemistry, Towards the Computational Design of Solid Catalysts," 2009, 1, pp. 37-46. (Year: 2009).

* cited by examiner

*Primary Examiner* — Paul A Zucker
(74) *Attorney, Agent, or Firm* — Blank Rome LLP (57) ABSTRACT

A continuous flow process for the preparation of one or more esters of lactic acid and 2-hydroxy-3-butenoic acid or α-hydroxy methionine analogs from a sugar in the presence of a solid Lewis acid catalyst and a solvent comprising an organic solvent and water. The invention facilitates Lewis acid catalyst stability in a continuous reaction process where the water is present in an amount of up to or equal to 10 vol. % of the organic solvent.

18 Claims, 7 Drawing Sheets

Fig. 9

PROCESS FOR PREPARING ESTERS OF LACTIC ACID, AND 2-HYDROXY-3-BUTENOIC ACID FROM SUGARS

CROSS REFERENCE TO RELATED APPLICATIONS

This is a continuation of U.S. patent application Ser. No. 15/525,450, filed May 9, 2017, now U.S. Pat. No. 10,100,007, which is a 371 of PCT/EP2015/076399, filed Nov. 12, 2015, which claims priority to Denmark Application No. PA 2015 00288, filed May 13, 2015 and European Application No. 14195485.9, filed Nov. 28, 2014, the entire disclosures of which are incorporated by reference in their entireties herein.

BACKGROUND OF THE INVENTION

1. Field of the Invention

The present invention relates to a novel process for the production of esters of lactic acid and 2-hydroxy-3-butenoic acid or α-hydroxy methionine analogues suitable for continuous flow processes.

2. Description of the Related Art

Carbohydrates represent the largest fraction of biomass and various strategies for their efficient use as a feedstock for the preparation of commercial chemicals are being established. Biomass is of particular interest due to its potential for supplementing, and ultimately replacing, petroleum. One such commercial chemical obtainable from biomass is lactic acid. A lactic acid derivative, methyl lactate, is a convenient building block towards renewable and biodegradable solvents and polymers.

Lactic acid derivatives, in particular esters of lactic acid, may be obtainable from sugars via a variety of reaction process routes including biochemical (enzymatic fermentation; enantiopure product), and synthetic (catalytic conversion; racemic product). Particular attention has been focused on synthetic (catalytic) routes as they provide a commercially and environmentally advantageous alternative to biochemical routes, in addition to providing a racemic product. A racemic product is advantageous if, for example, polymers that require stoichiometric amounts of both enantiomers of lactic acid enantiomers are desired as the starting materials, for example, polylactic acid (PLA).

The prior art establishes that racemic mixtures of esters of lactic acid and 2-hydroxy-3-butenoic acid may be prepared from sugars in the presence of a Lewis acid catalyst.

Esters of lactic acid and 2-hydroxy-3-butenoic acid or α-hydroxy methionine analogues may be prepared by a batch or continuous flow process from sugars in the presence of a Lewis acid catalyst. Both Science (2010) 328, pp 602-605 and EP 2 184 270 B1 disclose batch reactions for the process wherein the solvent is methanol only or methanol and 2.5 wt % water. Both references also disclose a batch reaction where the solvent is water, consequently producing lactic acid (30%) from sucrose.

In order to obtain an industrially feasible process for preparing the esters described above, it is essential that the Lewis acid catalyst remains stable, i.e. active, for a prolonged process duration. It is a well-known problem that Lewis acid catalysts deactivate over time during a reaction and must be regenerated by calcination. Deactivation of the Lewis acid catalyst requires the process to be stopped and the catalyst to be isolated and regenerated by calcination for at least 12-18 hours. Science (2010) 328, pp 602-605 and EP 2 184 270 B1 disclose that for all batch reactions the catalyst is regenerated by calcination after 20 hours.

Figure 7:
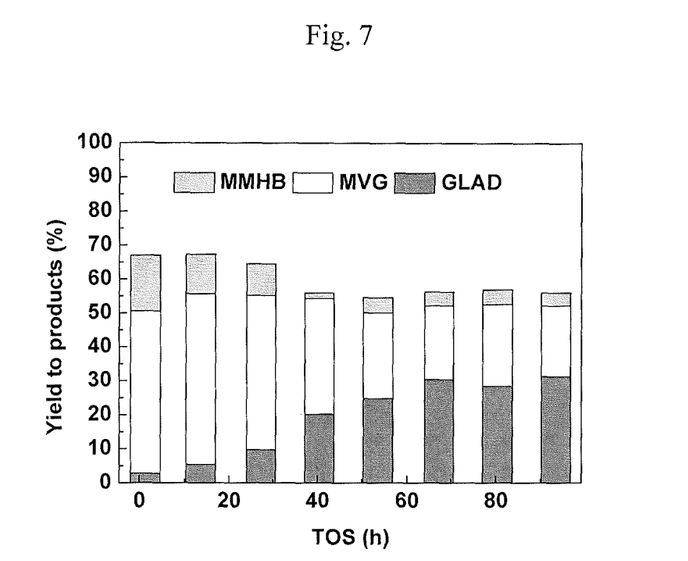

Science (2010) 328, pp 602-605 also discloses a continuous flow process for the conversion of a sugar (fructose) to methyl lactate in the presence of a Lewis acid catalyst (Sn-BEA) and an organic solvent (methanol). FIG. 7 of the supporting data indicates that the percentage yield of methyl lactate from fructose with time on stream (TOS) is reduced by at least 50%, from about 23% at 3 hours to about 11% at 80 hours. This figure shows that Sn-BEA deactivates gradually as a function of time on stream. Similarly to the batch reactions, the catalyst is regenerated by calcination. It is noted that Sn-BEA and Sn-Beta (as used here) are identical.

Additionally, Science (2010) 328, pp 602-605 illustrates that the presence of water to the reaction process is a disadvantage with regard to catalyst stability. When the solvent of the process is only water, the carbon deposition on the catalyst is greatly increased, contributing significantly to the deactivation of the catalyst. For example, when the solvent of the process is water, 7 wt % of carbon per gram of catalyst is deposited on the catalyst, in comparison to 1.3 wt % when the process employs methanol only as the solvent.

A further example of the disadvantage of the addition of water to a process that employs a Lewis acid catalyst has been reported in Journal of Catalysis (2003) 220, pp 326-332. This reference discloses the Mukiyama-type aldol condensation of aldehydes with a silyl enol ether over a titanium silicate Lewis acid catalyst (Ti-BETA or TS-1). The reference reports that the addition of a small amount of water to the batch reaction medium during the initial reaction period decreases the activity of the catalyst. It is believed that the Lewis acid catalysts are poisoned by water and therefore become inactive. For alternative reactions, ChemSusChem (2014) 7, pp 2255-2265, reports the same effect for Sn-BEA catalysed batch reactions.

A still further example of the disadvantage of the addition of water to a process that employs a Lewis acid catalyst has been reported in Journal of Catalysis (2014) 311, pp 244-256. This reference is directed towards the study of reaction pathways of the catalytic deoxygenation of propanal (propionaldehyde). The reference discloses that Lewis acid sites of the catalyst are prevented from participating in the catalytic reaction when water is present because the water rehydrates or is physisorbed onto these sites.

It is an object of the present invention to provide a means for stabilising a Lewis acid catalyst for use in a continuous reaction process for preparing esters of lactic acid and 2-hydroxy-3-butenoic acid from a sugar. It is a further object of the present invention to provide esters of lactic acid and α-hydroxy methionine analogues from a sugar.

In addition to reducing carbon deposition on the catalyst, it is a further object of the present invention to provide a means for stabilising a Lewis acid catalyst comprising Sn, wherein leaching of Sn from the catalyst is reduced and a significantly higher yield of esters of 2-hydroxy-3-butenoic acid is obtained. The reduction in Sn leaching results in a more pure product and a cheaper process (as less Sn is required). In addition, the esters of 2-hydroxy-3-butenoic acid by-product are valuable chemicals and may provide an additional commodity from the process. More explicitly, the addition of a significantly increased yield of esters of 2-hydroxy-3-butenoic acid provide a higher combined yield of esters of lactic acid and 2-hydroxy-3-butenoic acid, together with providing a higher conversion of the sugar. These advantages also apply to the preparation of the α-hydroxy methionine analogues.

DESCRIPTION OF THE INVENTION

It has now been discovered that the presence of water in the organic solvent of a continuous flow reaction facilitates Lewis acid catalyst stability for continuous flow reactions. Deposition of carbonaceous species on the catalyst leading to deactivation or poisoning of the catalyst Lewis acid active sites is not observed to any industrially significant extent. Retention in activity, i.e. stability of the catalyst, results in the continued high yields of the desired product for sustained reaction durations of continuous flow reactions.

The present invention relates to a continuous flow process for the preparation of one or more esters of lactic acid and 2-hydroxy-3-butenoic acid or α-hydroxy methionine analogues from a sugar in the presence of a solid Lewis acid catalyst and a solvent comprising an organic solvent and water, wherein the water is present in an amount of up to or equal to 10 vol. % of the organic solvent.

If an α-hydroxy methionine analogue is desired, a compound comprising sulfur needs to be present in addition to a solid Lewis acid catalyst and a solvent comprising an organic solvent and water.

Continuous flow process means a reaction or process that occurs over a (prolonged) period of time and the reactant is fed through a reaction chamber in a solvent. A general reference demonstrating continuous flow processes is Perry's Chemical Engineers' Handbook, eighth edition, McGraw-Hill, 2008.

The terms continuous flow process, process, reaction and reaction process are intended to be interchangeable.

More specifically, the present invention relates to a continuous flow process wherein the amount of water present in the solvent is up to 10 volume percent (vol. %) of the organic solvent. Volume percent means a volume to volume ratio of two solvents; for example, 10 volume % means a ratio of 10:90 of a first solvent and a second solvent. For example, in the present invention 10 volume % of water in an organic solvent means a volume ratio of 10:90 of water to an organic solvent. The invention may be performed where the vol. % of water present in the organic solvent is from greater than 0 to 30 vol. % or from greater than 0 to 20 vol. %. In a preferred embodiment, the vol. % of water present in the organic solvent is from greater than 0 to equal to or less than 10 vol. %. For example, the vol. % of water present in the organic solvent may be about 5 vol. %, about 1 vol. % or about 0.25 vol. %.

In an embodiment of the invention, the vol. % of water present in the organic solvent may be chosen to influence the yield of either the esters of lactic acid or the esters of 2-hydroxy-3-butenoic acid or α-hydroxy methionine analogues produced. For example, where the vol. % of water present in the organic solvent is from greater than 0 to 2 vol. %, the optimal yield of esters of lactic acid may be obtained. Additionally, where the vol. % of water present in the organic solvent is from 3 to 10 vol. %, the optimal yield of esters of 2-hydroxy-3-butenoic acid (MVG) may be obtained.

The present invention also relates to the use of a sugar syrup as feed. Sugar syrups are low cost mixtures of sugar and water which constitute a particularly useful feedstock for the present invention. In one embodiment, sugar syrup is mixed with an organic solvent to provide the final reaction mixture containing sugar, water and the organic solvent. The water content may optionally be adjusted by choice of syrup concentration or by addition of more water independently of the syrup. The sugar syrups have a sugar dry matter content of higher than 30%, more preferably higher than 50% or yet more preferably higher than 64%. The term "sugar" refers to mono- and disaccharides and it can be selected from the group consisting of glycolaldehyde, glyceraldehyde, dihydroxyacetone, erythrose, erythrulose, threose, xylose, arabinose, glucose, fructose, mannose, galactose, sucrose, lactose, maltose and mixtures thereof. Examples of sugar syrups are dextrose syrup, high fructose corn syrup, sugar cane juice syrups, inverted sucrose syrup, sugar beet juice syrup (thick juice), hemicellulose syrups (containing mixtures of xylose, glucose, mannose and other sugars) and glycolaldehyde syrups (primarily containing glycolaldehyde, obtained e.g. as described in WO 2014/131743).

Organic solvent means one or more solvents selected from the group consisting of methanol, ethanol, 1-propanol, 1-butanol and isopropanol.

Esters of lactic acid and 2-hydroxy-3-butenoic acid means one or more esters of lactic acid and one or more esters of 2-hydroxy-3-butenoic acid. For example, if the organic solvent of the process is methanol only, then only the methyl ester of lactic acid and 2-hydroxy-3-butenoic acid would be formed.

The present invention additionally relates to a process wherein the yield of the one or more lactic acid esters decreases over the course of the continuous flow process. For example, the yield of the one or more lactic acid esters may decrease by up to 0.01, 0.02, 0.03, 0.05, 0.10, 0.15, 0.20 or 0.25% per hour on stream on average.

Decrease in yield per hour on stream on average means the decrease in the percentage yield of the one or more lactic acid esters over a period of time, once the continuous flow process has reached a steady state, divided by the number of hours in that period. For example: for a process that has reached a steady state, a 5% decrease in yield of one or more lactic acid esters from, for example from 50% to 45%, is observed over a period of 100 hours, corresponding to a decrease of 0.05% yield per hour on stream on average.

The decrease in the yield of the one or more lactic acid esters may also be expressed by the decrease in yield after a time period on stream, in particular once the process has reached a steady state. For example, the yield of one or more lactic acid esters may decrease by up to and including 5% in total after 50, 100, 150, 200, 250, 300, 400, 500 or 6000 hours on stream. This example is directly related to the process described in Example 1; the variation of the time may vary and is likely to depend on the process and industrial scale.

Steady state means that continuous flow process conditions have reached a constant state; e.g. the flow of solvent and reactants through the reaction chamber is consistent. This can be determined, for example, in the observation that the yield of the one or more lactic acid esters does not increase by about 5% over a period of about 5 h. This example is directly related to the process in Example 1 and is for illustrative purposes; the variation of the yield is likely to depend on the process and industrial scale and is not intended to limit the invention.

Time (hours) on stream (TOS) means time that the feed has passed through the catalyst bed.

The present invention also relates to a process wherein the yield of the one or more lactic acid esters or the combined yield of both the esters of lactic acid and 2-hydroxy-3-butenoic acid is greater than 40% after 50 hours on stream.

For example: the yield of the one or more lactic acid esters is greater than 40% after 50, 100, 150, 200, 250, 300, 400 or 500 hours on stream.

The present invention also relates to a process wherein the yield of the one or more lactic acid esters or the combined yield of both the esters of lactic acid and 2-hydroxy-3-butenoic acid is greater than 40% after 50 hours on stream. For example: the yield of the one or more lactic acid esters is greater than 40%, 45%, 50%, 55%, 60%, 65%, 70% or 75% after 50 hours on stream.

In a further embodiment of the present invention, a compound comprising sulfur is added to the process if it is desired to obtain an α-hydroxy methionine analogue.

The compound comprising sulfur is selected from the group consisting of $C_1$-$C_5$ alkyl thiol, $C_1$-$C_5$ alkyl thiol salts, dimethylmercaptan and dimethyl disulfide. $C_1$-$C_5$ alkyl thiol means mono- and di-substituted thiols with a substituent comprising straight or branched chain saturated aliphatic alkyl group comprising one, two, three, four or five carbons. Specifically, $C_1$-$C_5$ alkyl thiol means an alkyl thiol selected from the group consisting of methane thiol, ethane thiol, straight or branched chain propane thiol, straight or branched chain butane thiol and straight or branched chain pentane thiol.

$C_1$-$C_5$ alkyl thiol salt means the alkali or alkaline earth metal salt of a $C_1$-$C_5$ alkyl thiol. Specifically, $C_1$-$C_5$ alkyl thiol salt means a $C_1$-$C_5$ alkyl thiol in the salt form wherein the cation is selected from the group consisting of sodium, potassium, lithium, magnesium and calcium. Specifically, $C_1$-$C_5$ alkyl thiol salt means a $C_1$-$C_5$ alkyl thiol selected from one or more of the group consisting of $NaSCH_3$, $KSCH_3$, $Ca(SCH_3)_2$ and $Mg(SCH_3)_2$.

The α-hydroxy methionine analogues are selected from the group consisting of 2-hydroxy-4-($C_{1-5}$alkylthio)butanoic acid, salts and esters thereof. $C_{1-5}$alkylthio corresponds to the $C_{1-5}$ alkyl thio compound comprising sulfur present in the process. Preferably, the α-hydroxy methionine analogues are selected from the group consisting of 2-hydroxy-4-(methylthio)butanoic acid, salts and esters thereof. Preferably, the α-hydroxy methionine analogues are selected from the group consisting of 2-hydroxy-4-(methylthio)-butanoic acid, alkali and alkaline earth metal salts and $C_{1-8}$ alkyl esters thereof.

$C_{1-8}$ alkyl esters means esters comprising the alkyl group selected from the group consisting of methyl, ethyl, propyl, butyl, isopropyl, isobutyl, pentyl, hexyl, heptyl, octyl and 2-ethylhexyl. Alkali and alkaline earth metal salts are salts of the acid wherein the salt cation is selected from the group I and group II metals.

In one embodiment of the invention the methionine α-hydroxy analogue is 2-hydroxy-4-(methylthio)butanoic acid.

In a second embodiment of the invention the methionine α-hydroxy analogues are selected from the group consisting of 2-hydroxy-4-(methylthio)butanoic acid methyl ester, 2-hydroxy-4-(methylthio)butanoic acid ethyl ester, 2-hydroxy-4-(methylthio)butanoic acid propyl ester, 2-hydroxy-4-(methylthio)butanoic acid butyl ester, 2-hydroxy-4-(methylthio)butanoic acid isopropyl ester, 2-hydroxy-4-(methylthio)butanoic acid pentyl ester, 2-hydroxy-4-(methylthio)butanoic acid hexyl ester, 2-hydroxy-4-(methylthio)butanoic acid heptyl ester, 2-hydroxy-4-(methylthio)butanoic acid octyl ester and 2-hydroxy-4-(methylthio)butanoic acid 2-ethylhexyl ester.

Addition of a sulfur compound to the reaction process results in the preparation of an α-hydroxy methionine analogue, as can be seen in Table 1, which summarizes batch reactions of the conversion of sugars to methionine α-hydroxy analogues.

The batch reactions are expected to be transferable to a continuous process corresponding to the process wherein 2-hydroxy-3-butenoic acid and esters thereof are prepared.

TABLE 1

Batch Reactions of the conversion of sugars to methionine α-hydroxy analogues. Amount of methanethiol: 25 mL (gas), erythrulose initial concentration 13 g/l, glucose initial concentration 16 g/l, glycolaldehyde (GA) initial concentration 16 g/l, MVG initial concentration 32 g/l. S-MVG means methyl 2-hydroxy-4-(methylthio)-butanoate

| Sugar | Catalyst | Solvent | S-MVG Yield (%) | Conversion (%) | Selectivity (%) | T. (° C.) | t. (h) |
|---|---|---|---|---|---|---|---|
| Erythrulose | Sn-BEA | A | 19.6 | 68.1 | 28.8 | 60 | 16 |
| Erythrulose | Sn-MFI | A | 23.7 | 81.3 | 29.1 | 100 | 4 |
| Erythrulose | Sn-BEA | EtOH | 13.5 | 68.7 | 19.7 | 100 | 4 |
| Glucose | Sn-BEA | A | 5.2 | 96.8 | 5.3 | 170 | 16 |
| GA | Sn-BEA | A | 14.6 | 41.9 | 34.9 | 120 | 16 |
| MVG | Sn-BEA | A | 0 | 0 | 0 | 100 | 4 |

T. = temperature;
t. = time
Solvent A: MeOH + 0.13 mmol $K_2CO_3$
GA = glycolaldehyde The present invention relates to a process in which the solid Lewis acid catalyst is calcined after 80 hours, after 450 hours, after 500 hours or after 6000 hours of the continuous flow process.

The invention may also be illustrated by the mass of sugar converted per mass of catalyst present. For example: The decrease in yield per hour of the one or more lactic acid esters is up to 0.25% when at least 0.45 g of sugar per g of catalyst has been converted; the decrease in yield of the one or more lactic acid esters decreases by up to 5% when at least 25 g of sugar per g of catalyst has been converted; the yield of the one or more lactic acid esters is greater than 40% when at least 25 g of sugar per g of catalyst has been converted, when at least 30 g sugar per g of catalyst has been converted, when at least 200 g sugar per g of catalyst have been converted or when at least 2500 g sugar per g of catalyst has been converted.

In the process according to the present invention the solid Lewis acid catalyst is a zeotype material or a siliceous porous material. A zeotype material is one in which the aluminum atoms of a zeolite material are partly or fully substituted by a metal (metal atoms) such as zirconium (Zr), titanium (Ti) and tin (Sn). Zeolite materials are crystalline alumino-silicates with a microporous crystalline structure, according to Corma et al., Chem. Rev. 1995, 95 pp 559-614. Alternatively, porous materials such as MCM-41 and SBA-15 can be used.

In the process of the invention, the solid Lewis acid catalyst framework structure is selected from the group consisting of BEA, MFI, FAU, MOR, FER and MWW and porous materials such as MCM-41 and SBA-15.

The present invention relates to a process wherein the solid Lewis acid comprises an active metal selected from one or more of the group consisting of Sn, Ti, Pb, Zr, Ge and Hf.

The solid Lewis acid catalyst is preferably selected from the group consisting of Sn-BEA, Sn-MFI, Sn-FAU, Sn-MOR, Sn-MWW, Sn-MCM-41 and Sn-SBA-15.

The amount of Sn lost is calculated as the loss of Sn from the solid Lewis acid catalyst at a point in time after the process has started, divided by the initial amount of Sn in the solid Lewis acid catalyst at the start of the process.

It is preferred that the solid Lewis acid catalyst comprises Sn and that the loss of Sn from the solid Lewis acid catalyst is less than or equal to 0.11% of the initial amount of Sn per hour on stream on average, preferably less than or equal to 0.05% of the initial amount of Sn per hour on stream, more preferably less than or equal to 0.02% of the initial amount of Sn per hour on stream.

The present invention relates to a process wherein the solid Lewis acid catalyst comprises Sn and the loss of Sn from the solid Lewis acid catalyst is less than or equal to 8% of the initial amount of Sn after 50 hours on stream, less than or equal to 50% of the initial amount of Sn after 400 hours on stream, preferably less than or equal to 40% of the initial amount of Sn after 400 hours on stream, preferably less than or equal to 15% of the initial amount of Sn after 400 hours on stream.

Preferably the yield of the one or more esters of 2-hydroxy-3-butenoic acid is greater than 10%, more preferably greater or equal to 12%.

In the process of the present invention, the sugar is preferably selected from one or more of the group consisting of glucose, fructose, mannose, sucrose, xylose, erythrose, erythrulose, threose and glycolaldehyde.

In some cases it is preferred that an alkaline earth metal or an alkali metal ion is present in the reaction process. When GA is used as feed, alkali is not required.

According to the present invention, the alkali can be obtained by the addition to the process of one or more compounds selected from the group consisting of $K_2CO_3$, $KNO_3$, KCl, KOH, potassium acetate ($CH_3CO_2K$), potassium lactate ($CH_3CH(OH)CO_2K$), NaCl, NaOH, $Na_2CO_3$, $Li_2CO_3$ and $Rb_2CO_3$.

In the present invention, the one or more esters of lactic acid are preferably selected from the group consisting of methyl lactate and ethyl lactate.

Experimental data for figures are collected in Examples 1 and 2. For the sake of clarity, data obtained in continuous flow mode are represented using figures, while results from batch experiments are collected in tables.

BRIEF DESCRIPTION OF THE DRAWINGS

FIGS. 1-5 cover the conversion of C6-sugars (fructose) in continuous flow mode.

FIGS. 1-3 refer to diminishing of Sn leaching and diminishing of catalyst deactivation.

FIGS. 4a, 4b and 5 demonstrate the improvement in MVG yield when water is present.

DETAILED DESCRIPTION OF THE FIGURES AND EXAMPLES

Figure 1:
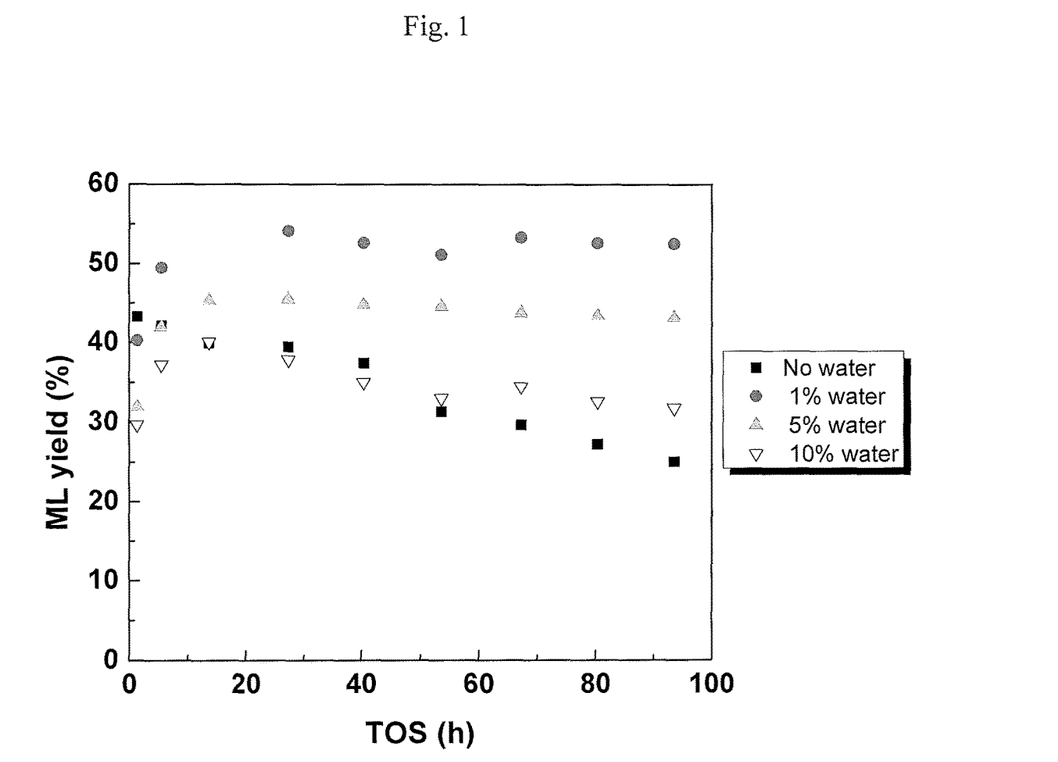

More specifically, the figures have the following meanings:

FIG. 1: Improved stability of the Sn-BEA Lewis acid catalysts with 1%, 5% and 10% water added to the process solvent compared to no water added to the process solvent. The catalyst stability is illustrated by a significantly consistent yield of methyl lactate product.

Figure 2:
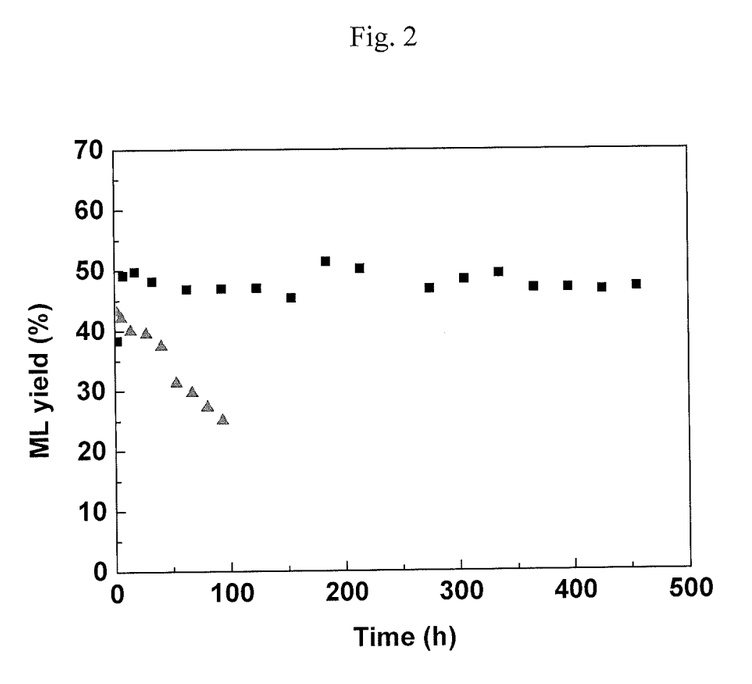

FIG. 2: Improved stability of the Sn-BEA Lewis acid catalysts with 1% water added to the process solvent (squares) compared to no water added to the process solvent (triangles). The catalyst stability is illustrated by a significantly consistent yield of methyl lactate product observed over a prolonged period of process time on stream (ca. 500 hours).

Figure 3:
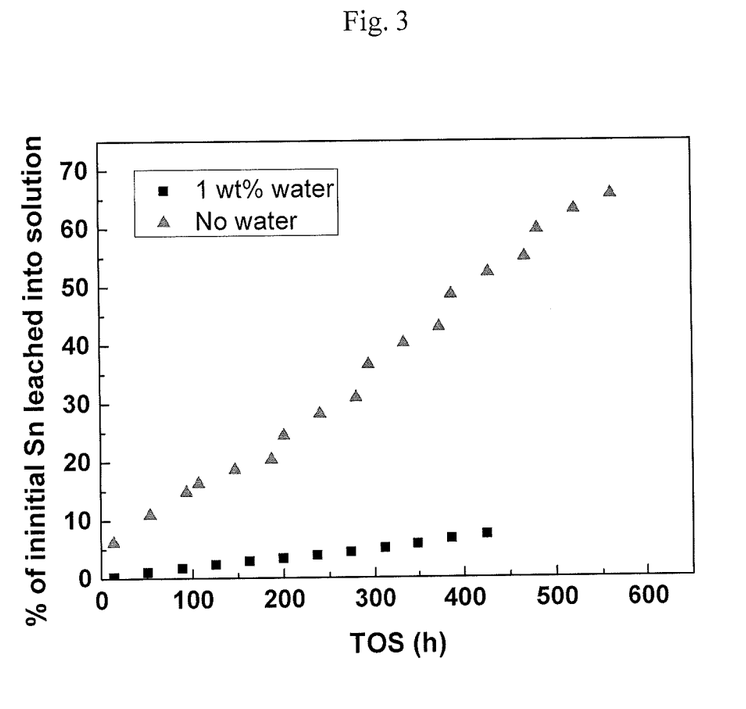

FIG. 3: Improved stability of the Sn-BEA Lewis acid catalysts with 1% water added to the process solvent (squares) compared to no water added to the process solvent (triangles). The improved stability is illustrated by a significant decrease of Sn leaching (loss of Sn) from the catalyst.

Figure 4A:
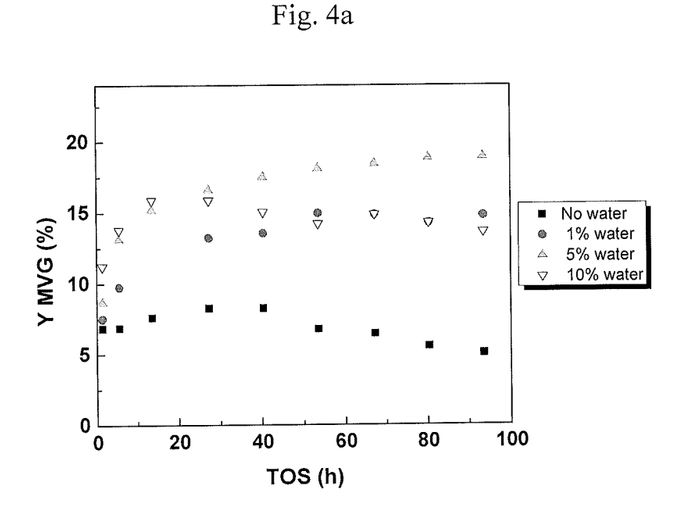
Figure 4B:
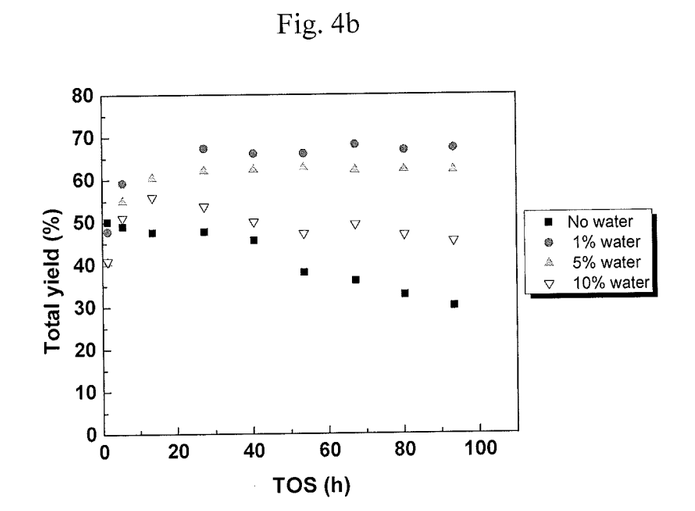

FIGS. 4a and 4b: Improved yield of esters of 2-hydroxy-3-butenoic acid with the addition of water to the continuous flow process: FIG. 4a Yield of 2-hydroxy-3-butenoic acid methyl ester (MVG); FIG. 4b Combined yield of esters of lactic acid (methyl lactate) and 2-hydroxy-3-butenoic acid methyl ester (MVG).

Figure 5:
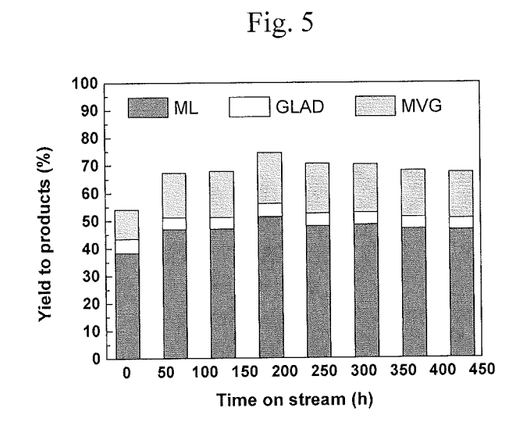

FIG. 5: Yield of bio-monomers obtained from fructose when using Sn-Beta zeolite in flow. Total yield [methyl lactate (ML), glycolaldehyde dimethyl acetal (GLAD) and methyl vinyl glycolate (MVG)] is 70% from fructose and it is stable over 400 h. Methyl vinyl glycolate (MVG) is equivalent to 2-hydroxy-3-butenoic acid methyl ester.

Figure 6:
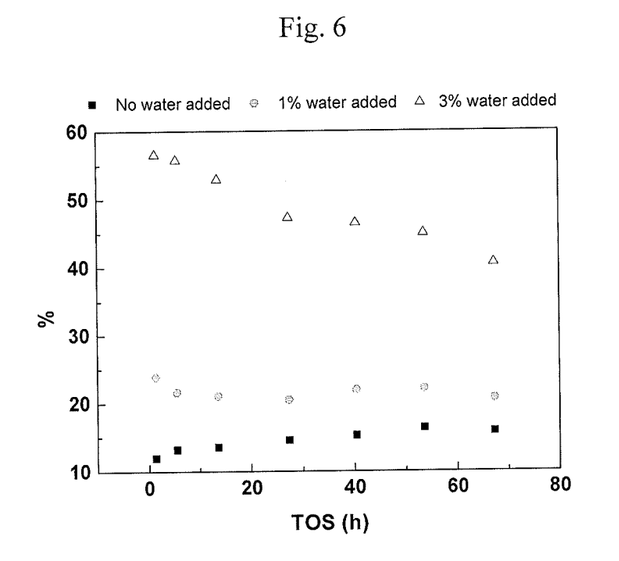
FIGS. 6-8 relate to the conversion of C2-sugar (glycolaldehyde) in continuous flow mode, with FIGS. 6 and 7 showing the improvement in MVG yield when water is present, and FIG. 8 showing the improvement in S-MVG yield when water and methanethiol are present.
Figure 8:
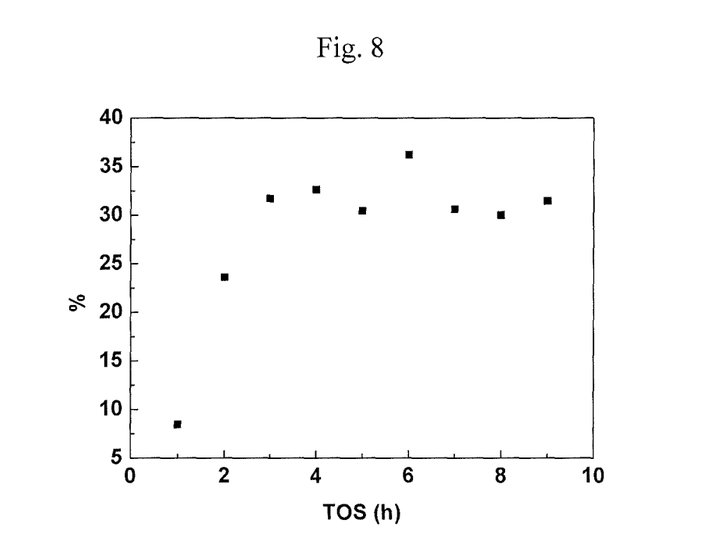

FIGS. 6-8 cover the conversion of C2-sugar (glycolaldehyde) in continuous flow mode. FIGS. 6 and 7 refer to the improvement in MVG yield when water is present. FIG. 8 refers to the improvement in S-MVG yield when water and methanethiol are present. More specifically, the figures have the following meanings:

FIG. 6: Improved yield of methyl vinyl glycolate (MVG) from glycolaldehyde with the addition of water in continuous flow mode. Feed composition: 20 g/l glycolaldehyde in methanol as solvent. Methyl vinyl glycolate (MVG) is equivalent to 2-hydroxy-3-butenoic acid methyl ester.

FIG. 7: Yield of bio-monomers obtained from glycolaldehyde when using Sn-Beta zeolite in flow. Feed composition: 20 g/l glycolaldehyde in methanol as solvent, 8.5 wt % water. Total yield [glycolaldehyde dimethyl acetal (GLAD), methyl vinyl glycolate (MVG) and methyl-4-methoxy-2-hydroxy-butenoate (MMHB)] is 65% from glycolaldehyde at the beginning of the reaction. Methyl vinyl glycolate (MVG) is equivalent to 2-hydroxy-3-butenoic acid methyl ester.

FIG. 8: Yield of methyl ester of α-hydroxy methionine analogue with Sn-BEA as catalyst in the presence of water and methanol in continuous flow reaction from glycolaldehyde. Feed composition: 9 g/l glycolaldehyde in methanol as solvent, 8.5 wt % water, 1.2 g/l methanethiol.

Figure 9:
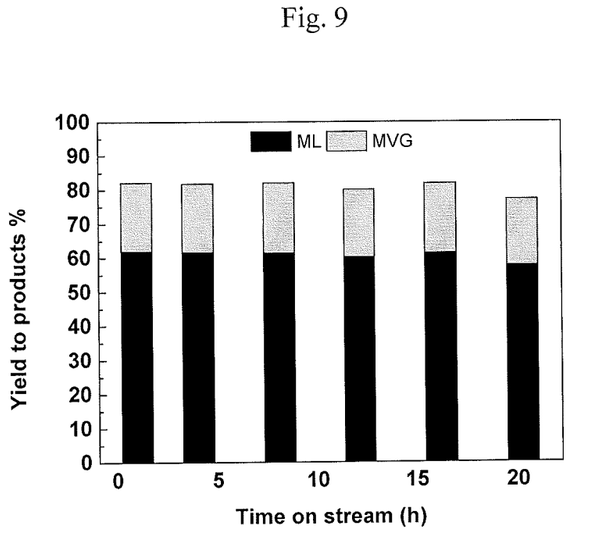
FIG. 9 relates to the use of syrup as feed in the reaction, showing the improvement in MVG yield when water is present and the use of sugar in the form of a sugar syrup.

FIG. 9 exemplifies the use of syrup as feed in the reaction. It demonstrates the improvement in MVG yield when water is present and the use of sugar in the form of a sugar syrup. More specifically, the figure has the following meaning:

FIG. 9: Yield of bio-monomers obtained from sucrose syrup when using Sn-Beta zeolite in flow. Feed composition: 55 g/l sucrose. The total yield [methyl lactate (ML), methyl vinyl glycolate (MVG)] is 80% from sucrose syrup and it is stable. Methyl vinyl glycolate (MVG) is equivalent to 2-hydroxy-3-butenoic acid methyl ester.

The process of the invention is illustrated further by the following examples.

Example 1

Preparation of Catalyst

Sn-BEA (Si/Sn=125) is prepared according to a modification of the procedure described in U.S. Pat. No. 4,933,161. Commercial zeolite Beta (Zeolyst, Si/Al 12.5, ammonium form) is calcined (550° C. for 6 h) to obtain the H form (de-aluminated form) and treated with 10 grams of concentrated nitric acid (Sigma-Aldrich, 65%) per gram of zeolite beta powder for 12 h at 80° C. The resulting solid is filtered, washed with ample water and calcined (550° C. for 6 h) to obtain the de-aluminated Beta. This solid is impregnated by incipient wetness methodology with a Sn/Si ratio of 125. For this purpose, tin (II) chloride (0.128 g, Sigma-Aldrich, 98%) is dissolved in water (5.75 ml) and added to the de-aluminated Beta (5 g). After the impregnation process, the samples are dried 12 h at 110° C. and calcined again (550° C. for 6 h).

Catalytic Reaction in Continuous Flow Mode:

Fructose (Sigma-Aldrich, 99%) was dissolved in methanol (Sigma-Aldrich, 99.9%) at room temperature to reach a concentration of 12.5 g/l. Additionally, deionized water (0, 10, 50 or 100 ml/l) and potassium carbonate (Sigma-Aldrich, 99%, 2.5 mg/l) were added to the feed solution. Catalyst Sn-Beta (Si:Sn 125) prepared according to the above preparation was fractionized (0.25 g, 300-600 µm.) and loaded into a stainless steel 0.25 inch reactor. Glass wool was used to hold the catalyst in place. The reactor was introduced into an oven and the temperature of the reactor increased to 160° C. When the temperature was over 140° C., the pump was started with a flow of 0.15 ml/min of a 1.25 wt. % fructose solution in methanol.

Glycolaldehyde (glycolaldehyde dimer, Sigma) was dissolved in methanol (Sigma-Aldrich, 99.9%) at room temperature to reach a concentration of 9 g/l. Additionally, deionized water (0, 10, 30 ml/l) and if necessary methanethiol (Sigma, 1.7 bar) were added to the feed solution. Catalyst Sn-BEA (Si:Sn 125) prepared according to the above preparation was fractionized (0.25 g, 300-600 µm) and loaded into a stainless steel 0.25 inch reactor. Glass wool was used to hold the catalyst in place. The reactor was introduced into an oven and the temperature of the reactor increased to 160° C. When the temperature was over 140° C., the pump was started with a flow of 0.05 ml/min (see FIG. 8).

Sucrose syrup (65 wt %, $KNO_3$ 1 g/l) and methanol (Sigma-Aldrich, 99.9%) were pumped separately and mixed at 160° C. to reach a sucrose concentration of 55 g/l. Catalyst Sn-BEA (Si:Sn 125) prepared according to the above preparation was extruded (40 g, 1/32" cylinders) and loaded into a stainless steel reactor. Glass wool was used to hold the catalyst in place. The reactor was introduced into an oven, and the temperature of the reactor increased to 160° C. (see FIG. 9).

Samples were collected after different times on stream and analysed by HPLC (Agilent 1200, Biorad Aminex HPX-87H column at 65° C., 0.05 M $H_2SO_4$, 0.6 ml/min) to quantify unconverted hexoses and dihydroxyacetone (DHA), glyceraldehyde (GLA); and GC (Agilent 7890 with a Phenomenex Solgelwax column) was used to quantity: methyl lactate (ML), methyl vinyl glycolate (MVG, methyl 2-hydroxy-3-butenoate), glycolaldehyde dimethylacetal (GLAD) and sulfur-methylvinyl-glycolate (S-MVG, methyl 2-hydroxy-4-(methylthio)-butanoate).

Example 2

Determination of the Total Amount of Soluble Tin in the Liquid Medium:

The determination of the total amount of soluble tin (Sn) was carried out using inductively coupled plasma mass spectrometry (ICP-MS). The methanol sample was diluted by weight with an 80/20 xylene/2-propanol mixture. The total Sn content is quantified by ICP-MS (Agilent 7500ce ICP-MS instrument) at the Sn isotope masses 118 and 120 by comparison with a calibration curve made from a 900 ppm Conostan organo-metallic Sn standard diluted with xylene. Indium is used as an internal standard to correct for drift and matrix effects. Removal of molecular interferences in the ICP-MS analysis is done with Helium kinetic energy discrimination. EnviroMAT "Used oil" certified reference standard which gives an informational value for Sn (305 mg/kg) is analyzed with each sample batch to verify the precision of the method.

Example 3

This example illustrates the conversion of C2-sugars (glycolaldehyde) to MVG with increased yield due to the effect of water in batch experiments.

Catalytic Reactions in Batch:

A stainless steel pressure vessel (40 cm$^3$, Swagelok) was charged with 15.0 g of methanol (Sigma-Aldrich, >99.8%), the required amount of water, 0.200 g glycolaldehyde (glycolaldehyde dimer, Sigma) and 0.150 g of catalyst. The reactor was closed and heated to 160° C. under stirring (900 rpm). The reaction was continued for 16 hours, and after this period, the reaction was quenched by submerging the vessel in cold water. Samples from the reaction vessel were filtered and analyzed by HPLC (Agilent 1200, Biorad Aminex HPX-87H column at 65° C., 0.05 M $H_2SO_4$, 0.5 ml/min) to quantify unconverted glycolaldehyde (GA); and GC (Agilent 7890 with a Phenomenex Solgelwax column was used to quantify the following: Methyl lactate (ML), methyl vinylglycolate (MVG, methyl-2-hydroxy-3-butenoate), glycolaldehyde dimethylacetal (GLAD) and methyl-4-methoxy-2-hydroxybutanoate (MMHB).

Table 2 shows the effect of the amount of water in batch experiments from glycolaldehyde using Sn-Beta in methanol. An improved yield of methyl vinylglycolate (MVG) and methyl-4-methoxy-2-hydroxybutanoate (MMHB) is obtained with the addition of water to the batch reaction. Methyl vinylglycolate (MVG) is equivalent to 2-hydroxy-3-butenoic acid methyl ester.

TABLE 2

Effect of the amount of water in batch experiments from glycolaldehyde using Sn-BEA in methanol

| Batch exp. No | Wt % water | GLAD yield | MVG yield | MMHB yield | Total C4 yield |
|---|---|---|---|---|---|
| 1 | 0 | 35% | 32% | ~11% | 43% |
| 2 | 3 wt % | 0 | 52% | ~14% | 67% |
| 3 | 8.5 wt % | 0 | 55% | ~15% | 70% |
| 4 | 21 wt % | 0 | 46% | ~12% | 58% |

In Table 3, the effect of the presence (amount) of alkali in batch experiments from glycolaldehyde using Sn-Beta in methanol is shown. An improved yield of methyl vinylglycolate (MVG) and methyl-4-methoxy-2-hydroxybutanoate (MMHB) is obtained with the addition of water to the batch reaction in the absence of alkali. This experiment shows that water is the component responsible for the increase in yields, while the presence of alkali is less important. It is, however, preferred to operate in the absence of alkali. The results in batch experiment No. 7 are comparable to conditions mentioned in Green Chemistry 2012, 14, p. 702. Results from said paper: ML 16%, MVG 27%, MMHB 6%.

TABLE 3

Effect of the presence (amount) of alkali in batch experiments from glycolaldehyde using Sn-BEA in methanol

| Batch exp. No | Water wt % | mM $K_2CO_3$ in MeOH | GLAD yield | ML yield | MVG yield | MMHB yield | Total C4 yield |
|---|---|---|---|---|---|---|---|
| 3 | 8.5 | 0 | 0 | 0 | 55% | ~15% | 70% |
| 6 | 8.5 | 0.13 | 0 | 0 | 48% | ~16% | 66% |
| 1 | 0 | 0 | 35% | 0 | 32% | ~11% | 43% |
| 7 | 0 | 0.13 | 0 | 13% | 37% | ~15% | 52% |

Table 4 shows the effect of the type of catalyst in batch experiments from glycolaldehyde using different stannosilicates in methanol. Optimum yield of methyl vinylglycolate (MVG) and methyl-4-methoxy-2-hydroxybutanoate (MMHB) is obtained with Sn-BEA as catalyst.

TABLE 4

Effect of the type of catalyst in batch experiments from glycolaldehyde using Sn-silicates in methanol

| Batch exp. No | Catalyst | GLAD yield | ML yield | MVG yield | MMHB yield | Total C4 yield |
|---|---|---|---|---|---|---|
| 3 | Sn-Beta | 0 | 0 | 55% | ~15% | 70% |
| 8 | Sn-SBA-15 | 8% | 3% | 2% | 2% | 4% |
| 9 | Sn-MCM-41 | 1% | 6% | 6% | 8% | 14% |

Example 4

This example relates to catalytic reactions in batch to produce sulfur-methyl vinylglycolate (S-MVG, methyl 2-hydroxy-4-(methylthio)-butanoate) and sulfur-ethyl vinylglycolate (S-EVG, ethyl 2-hydroxy-4-(methylthio)-butanoate) from C2-sugars (glycolaldehyde).

1.6 g of an aqueous solution containing glycolaldehyde (34.2 g/l) produced from commercial glycolaldehyde (Glycolaldehyde dimer, Sigma) or obtained from fragmentation of a 40 wt % glucose syrup (WO 2014/131743) was mixed either with pure methanol (13.8 g; Sigma-Aldrich 99.9%) or with pure ethanol (13.8 g; CCS Healthcare 99.9%). Then 0.16 g of catalyst and the desired amount of methanethiol (Sigma, 1.7 bar) were added, and the mixture was reacted in a pressure reactor at 160° C. (temperature of the oil bath) with 900 rpm stirring under autogenous pressure. An initial sample of the reaction mixture was used for calculation of the conversion and the yields. Samples were collected after 16 h of reaction and analysed by HPLC (Agilent 1200, Biorad Aminex HPX-87H column at 65° C., 0.05 M $H_2SO_4$, 0.6 ml/min) to quantify unconverted C2 sugars and formed C4 sugars; and GC (Agilent 7890 with Phenomenex Solgelwax column) was used to quantify the following: Methyl vinylglycolate (MVG, methyl 2-hydroxy-3-butenoate), ethyl vinylglycolate (EVG, ethyl 2-hydroxy-3-butenoate), sulfur-methyl vinylglycolate (S-MVG, methyl 2-hydroxy-4-(methylthio)-butanoate) and sulfur-ethyl vinylglycolate (S-EVG, ethyl 2-hydroxy-4-(methylthio)-butanoate).

Table 5 shows batch reactions of the conversion of glycolaldehyde to esters of methionine α-hydroxy analogue with Sn-BEA as catalyst in the presence of water and solvent. Amount of methanethiol: 3.6 mmol. Optimum yield was obtained in methanol to S-EVG.

TABLE 5

Batch reactions of the conversion of glycolaldehyde to esters of methionine α-hydroxy analogue [Methyl vinylglycolate (MVG, methyl 2-hydroxy-3-butenoate), ethyl vinylglycolate (EVG, ethyl 2-hydroxy-3-butenoate), sulfur-methyl vinylglycolate (S-MVG, methyl 2-hydroxy-4-(methylthio)-butanoate) and sulfur-ethyl vinylglycolate (S-EVG, ethyl 2-hydroxy-4-(methylthio)-butanoate)]

| Batch exp. No | Solvent | Yield of α-hydroxy methionine analogue | MVG or EVG yield | Conversion | Selectivity |
|---|---|---|---|---|---|
| 10 | MeOH | 39.4% S-MVG | 13.9% (MVG) | 98.6 | 39.9% S-MVG |
| 11 | EtOH | 47.3% S-EVG | 19.5% (EVG) | 100 | 47.3% S-EVG |

Table 6 shows batch reactions of the conversion of glycolaldehyde to esters of methionine α-hydroxy analogue with Sn-Beta as catalyst in the presence of water and methanol. The results illustrate the effect of the GA/thiol molar ratio. Optimum yield to S-MVG is obtained with a molar ratio of 0.8.

TABLE 6

Batch reactions of the conversion of glycolaldehyde to esters of α-hydroxy methionine analogue (S-MVG, methyl 2-hydroxy-4-(methylthio)-butanoate)

| Batch experiment No | GA/thiol (molar ratio) | S-MVG yield | MVG yield |
|---|---|---|---|
| 10 | 0.8 | 37.5 | 7.3 |
| 12 | 0.6 | 33.6 | 0 |
| 13 | 1 | 30.6 | 7.3 |
| 14 | 5 | 18.1 | 33.1 |
| 16 | 0.2 | 8.3 | 0 |
| 17 | No thiol | 0 | 55.0 |

What is claimed is:

1. A continuous flow process for the preparation of one or more esters of lactic acid and 2-hydroxy-3-butenoic acid from a sugar selected from one or more of the group consisting of glucose, fructose, mannose, sucrose, xylose, erythrose, erythrulose, threose and glycolaldehyde, in the presence of a solid Lewis acid catalyst and a solvent comprising an organic solvent and water, wherein the volume % of water present in the organic solvent is from 0.25 vol % to 10 vol. %, wherein the solid Lewis acid catalyst has a framework structure, which is selected from the group consisting of BEA, MFI, FAU, MOR, FER, MWW, MCM-41 and SBA-15.

2. A process according to claim 1, wherein the yield of the one or more lactic acid esters decreases by up to 0.25% per hour on stream on average, wherein the yield is amount of ester relative to the amount of sugar.

3. A process according to claim 1, wherein the yield of the one or more lactic acid esters decreases by up to 0.10% per hour on average, wherein the yield is amount of ester relative to the amount of sugar.

4. A process according to claim 1, wherein the yield of the one or more lactic acid esters decreases by up to 5% after 50 hours on stream, wherein the yield is amount of ester relative to the amount of sugar.

5. A process according to claim 1, wherein the yield of the one or more lactic acid esters is greater than 40% after 50 hours on stream, wherein the yield is amount of ester relative to the amount of sugar.

6. A process according to claim 1, wherein the solid Lewis acid catalyst is calcined after 450 hours of continuous flow process.

7. A process according to claim 1, wherein the solid Lewis acid catalyst comprises an active metal selected from one or more of the group consisting of Sn, Ti, Pb, Zr, Ge and Hf.

8. A process according to claim 1, wherein the solid Lewis acid catalyst is selected from the group consisting of Sn-BEA, Sn-MFI, Sn-FAU, Sn-MOR, Sn-MWW, Sn-MCM-41 and Sn-SBA-15.

9. A process according to claim 1, wherein the solid Lewis acid catalyst comprises Sn and the loss of Sn from the solid Lewis acid catalyst is less than or equal to 0.11% of the initial amount of Sn per hour on stream.

10. A process according to claim 1, wherein the solid Lewis acid catalyst comprises Sn and the loss of Sn from the solid Lewis acid catalyst is less than 8% of the initial amount of Sn after 50 hours on stream.

11. A process according to claim 1, wherein the yield of 2-hydroxy-3-butenoic acid ester is greater than 12% after 50 hours on stream, wherein the yield is amount of ester relative to the amount of acid sugar.

12. A process according to claim 1, wherein an alkaline earth metal or alkali metal ion is present in the process.

13. A process according to claim 1, wherein the solvent is selected from one or more of the group consisting of methanol, ethanol, 1-propanol, 1-butanol and isopropanol.

14. A process according to claim 1, wherein the temperature of the process is from 140° C. to 200° C.

15. A process according to claim 1, wherein at least a fraction of the water is introduced to the solvent by mixing the organic solvent with an aqueous sugar solution.

16. A process according to claim 1, wherein the aqueous sugar solution is a sugar syrup with a sugar dry matter content of 30% or higher.

17. A continuous flow process for the preparation of one or more esters of lactic acid and 2-hydroxy-3-butenoic acid from a sugar selected from one or more of the group consisting of glucose, fructose, mannose, sucrose, xylose, erythrose, erythrulose, threose and glycolaldehyde, in the presence of a solid Lewis acid catalyst and a solvent comprising an organic solvent and water, wherein the vol. % of water present in the organic solvent is from 0.25 to 10 vol. %, and wherein the solid Lewis acid catalyst is Sn-BEA.

18. A continuous flow process for the preparation of one or more esters of lactic acid and 2-hydroxy-3-butenoic acid from a sugar selected from one or more of the group consisting of glucose, fructose, mannose, sucrose, xylose, erythrose, erythrulose, threose and glycolaldehyde, in the presence of a solid Lewis acid catalyst and a solvent comprising an organic solvent and water, wherein the vol. % of water present in the organic solvent is from 0.25 to 10 vol. % and at least a fraction of the water is introduced to the solvent by mixing the organic solvent with an aqueous sugar solution, and wherein the solid Lewis acid catalyst is Sn-BEA.

* * * * *